(12) United States Patent
Woehl et al.

(10) Patent No.: US 10,060,946 B2
(45) Date of Patent: Aug. 28, 2018

(54) ELECTRON VIBROMETER AND DETERMINING DISPLACEMENT OF A CANTILEVER

(71) Applicant: The United States of America, as represented by the Secretary of Commerce, Washington, DC (US)

(72) Inventors: Taylor J. Woehl, Golden, CO (US);
Ryan B. Wagner, Boulder, CO (US);
Jason Killgore, Boulder, CO (US);
Robert Keller, Louisville, CO (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/449,419

(22) Filed: Mar. 3, 2017

(65) Prior Publication Data
US 2017/0261533 A1 Sep. 14, 2017

Related U.S. Application Data

(60) Provisional application No. 62/305,082, filed on Mar. 8, 2016.

(51) Int. Cl.
*G01Q 20/00* (2010.01)
*G01B 15/00* (2006.01)
*G01N 23/22* (2018.01)

(52) U.S. Cl.
CPC ............ *G01Q 20/00* (2013.01); *G01B 15/00* (2013.01); *G01N 23/22* (2013.01)

(58) Field of Classification Search
USPC .............. 850/9, 8, 5; 250/306, 307, 310
See application file for complete search history.

(56) References Cited

U.S. PATENT DOCUMENTS

| 5,289,004 A | * | 2/1994 | Okada | B82Y 35/00 |
| | | | | 250/423 F |
| 2008/0055607 A1 | * | 3/2008 | Moon | B82Y 10/00 |
| | | | | 356/508 |

OTHER PUBLICATIONS

Schroter, M-A., et al., Phase and amplitude patterns in DySEM mappings of vibrating microstructures, Nanotechnology, 2013, 215701, 24.

(Continued)

*Primary Examiner* — Kiet T Nguyen
(74) *Attorney, Agent, or Firm* — Office of Chief Counsel for National Institute of Standards and Technology

(57) ABSTRACT

An electron vibrometer includes: an electron source providing a beam of primary electrons; a cantilever including: a receiver portion including: a gradient in thickness, a gradient in mass, atomic number of constituent atoms, or a combination thereof, the cantilever being disposed relative to the electron source such that the receiver portion of the cantilever receives the beam of primary electrons, and produces a plurality of scattered electrons from the receiver portion in response to receipt of the beam of primary electrons; and a charged particle detector that receives the plurality of scattered electrons from the receiver portion, and produces a detector signal comprising an amplitude that varies in relation to the gradient subject to receipt of the primary electrons, and the detector signal providing determination of the displacement of the cantilever.

20 Claims, 14 Drawing Sheets

(56) References Cited

OTHER PUBLICATIONS

Sturm, H., et al., Imaging method for vibrating scanning force microscopy cantilevers for the analysis of mode shapes and non-linear harmonic motion, Microelectronic Engineering, 2012, 492-496, 98.

* cited by examiner (A)

(B)

US 10,060,946 B2

ELECTRON VIBROMETER AND DETERMINING DISPLACEMENT OF A CANTILEVER

CROSS REFERENCE TO RELATED APPLICATIONS

This application claims the benefit of U.S. Provisional Patent Application Ser. No. 62/305,082, filed Mar. 8, 2016, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is an electron vibrometer to determine a displacement of a cantilever, the electron vibrometer comprising: an electron source providing a beam of primary electrons; the cantilever comprising: a receiver portion comprising: a gradient in thickness, a gradient in mass, a gradient in atomic number of constituent atoms, or a combination comprising at least one of the foregoing gradients, the cantilever being disposed relative to the electron source such that the receiver portion of the cantilever receives the beam of primary electrons, and produces a plurality of scattered electrons from the receiver portion in response to receipt of the beam of primary electrons; and a charged particle detector that receives the plurality of scattered electrons from the receiver portion, and produces a detector signal comprising an amplitude that varies in relation to the gradient subject to receipt of the primary electrons, and the detector signal providing determination of the displacement of the cantilever.

Also disclosed is a process for determining a displacement of a cantilever, the process comprising: providing a beam of primary electrons; subjecting the cantilever at a receiver portion to the beam of primary electrons, the cantilever comprising: the receiver portion comprising: a gradient in thickness, a gradient in mass, a gradient in atomic number of constituent atoms, or a combination comprising at least one of the foregoing gradients, receiving the beam of primary electrons at receiver portion of the cantilever; producing a plurality of scattered electrons from the receiver portion in response to receiving the beam of primary electrons; receiving the scattered electrons at a charged particle detector; producing, by the charged particle detector, a detector signal comprising an amplitude that varies in relation to the gradient present in the receiver potion to determine the displacement of the cantilever.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that an electron vibrometer provides detection of a displacement of a cantilever (e.g., an atomic force microscope (AFM) cantilever) with beam of electrons. Advantageously, the electron vibrometer can be used in a scanning electron microscope (SEM). Unexpectedly, detecting scattered electrons by the electron vibrometer provides imaging of the cantilever that is, e.g., 100 times smaller than conventional cantilevers and that oscillates with a higher frequency than that of conventional cantilevers. Beneficially, the electron vibrometer uses electrons to determine the displacement of cantilever in an absence or presence of an optical detection system (e.g., a laser and photodiode) that is conventionally used to detect motion of AFM cantilever.

Figure 1:
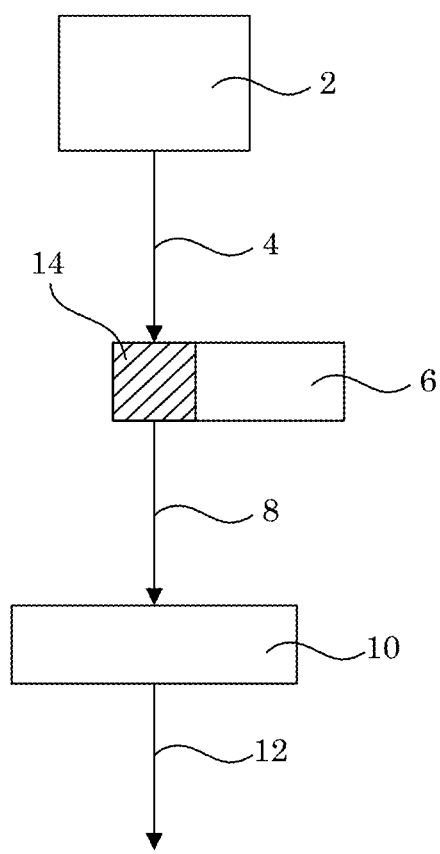
FIG. 1 shows an electron vibrometer.

The electron vibrometer determines a displacement of a cantilever. In an embodiment, with reference to FIG. 1, electron vibrometer 100 includes electron source 2 providing a beam of primary electrons 4; cantilever 6 that includes receiver portion 14 (including a gradient in thickness, a gradient in mass, a gradient in atomic number of constituent atoms, or a combination of the foregoing gradients), cantilever 6 being disposed relative to electron source 2 such that receiver portion 14 of cantilever 6 receives the beam of primary electrons 4, and produces a plurality of scattered electrons 8 from receiver portion 14 in response to receipt of the beam of primary electrons 4; and charged particle detector 10 that receives scattered electrons 8 from receiver portion 14. Moreover, charged particle detector 10 produces detector signal 12 that includes an amplitude that varies in relation to the gradient that is subject to receipt of primary electrons 4, and detector signal 12 provides determination of the displacement of cantilever 6. Here, receiver portion 14 of cantilever 6 oscillates relative to the beam of primary electrons 4, electron source 2, charged particle detector 10, or a combination thereof. In an embodiment, cantilever 6 oscillates relative to electron source 2.

Figure 2:
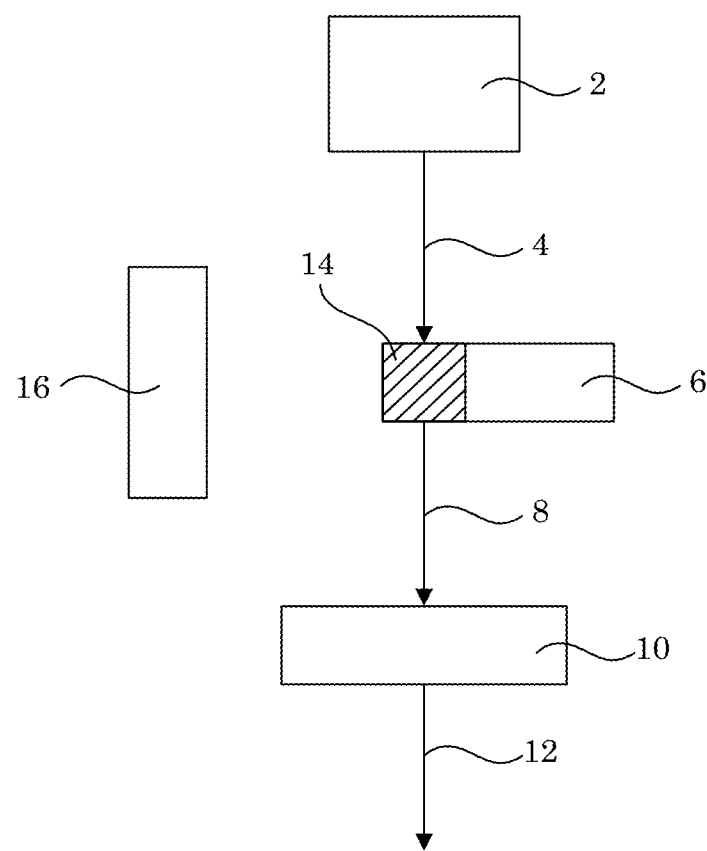
FIG. 2 shows an electron vibrometer.

In an embodiment, with reference to FIG. 2, electron vibrometer 100 includes sample 16 disposed proximate to cantilever 6 and arranged to interact with cantilever 6. Here, receiver portion 14 of cantilever 6 oscillates relative to the beam of primary electrons 4, electron source 2, charged particle detector 10, or a combination thereof. In an embodiment, cantilever 6 oscillates relative to electron source 2.

Figure 3:
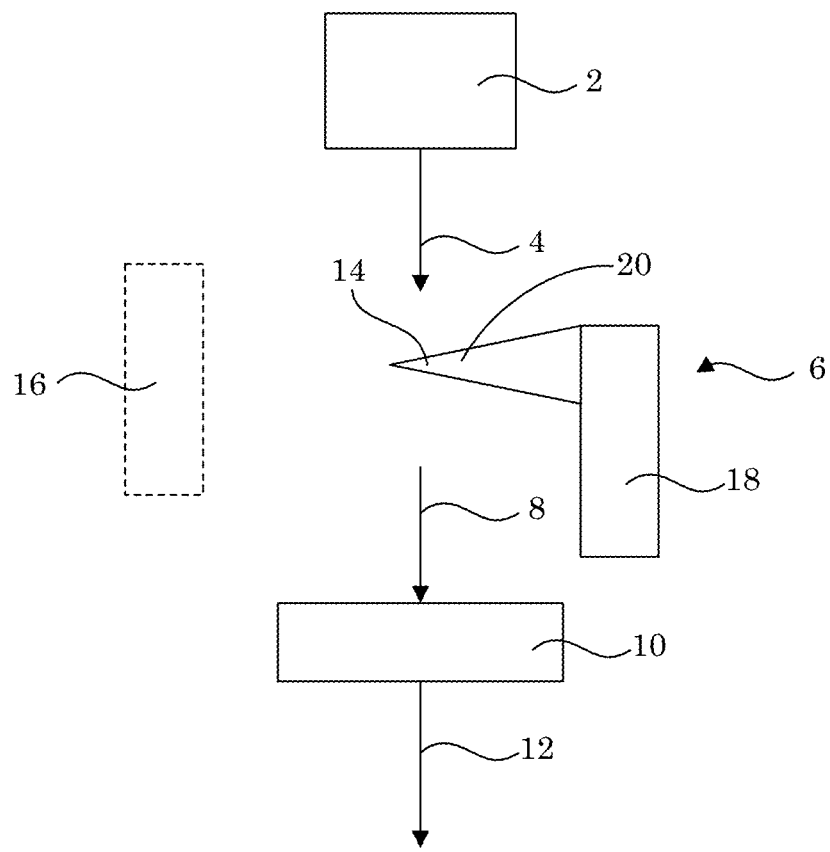
FIG. 3 shows an electron vibrometer.
Figure 4:
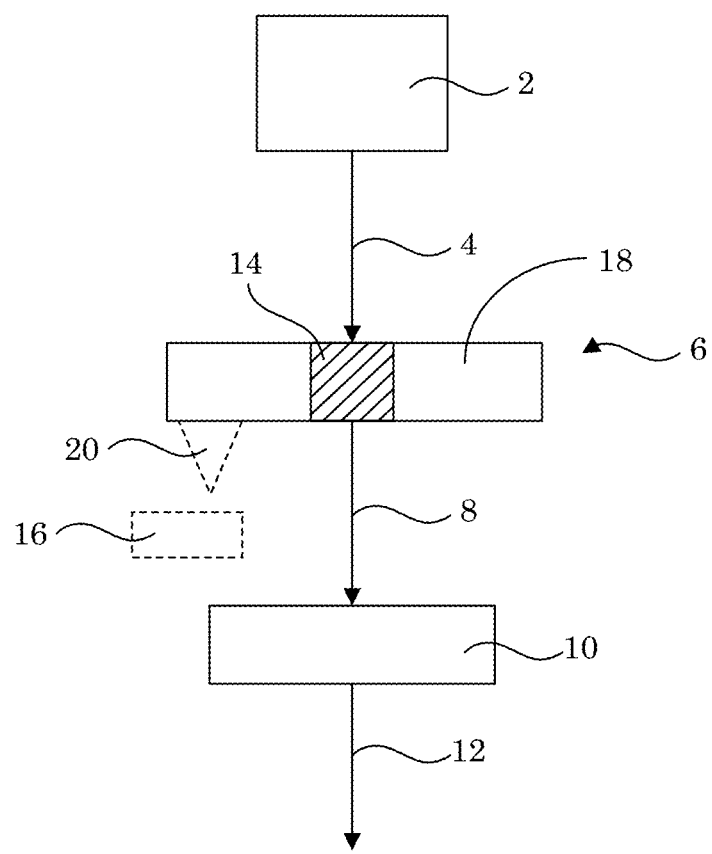
FIG. 4 shows an electron vibrometer.
Figure 4:
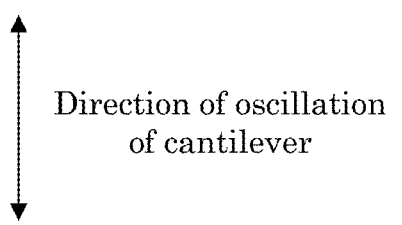

In an embodiment, with reference to FIG. 3 and FIG. 4, cantilever 6 includes body member 18 and tip 20 disposed on body member 18. It is contemplated that tip 20 can include receiver portion 14 subject to receipt of primary electrons 4 and production of scattered electrons 8 as shown in FIG. 3. In some embodiments, body member 18 includes receiver portion 14 that is subject to receipt of primary electrons 4 and production of scattered electrons 8 as shown in FIG. 4.

In an embodiment, scattered electrons 8 include transmitted electrons, and charged particle detector 10 includes a transmitted electron detector. Here, transmitted electron detector 10 can be disposed opposing electron source 2, and receiver portion 14 of cantilever 6 is interposed between electron source 2 and transmitted electron detector 10.

Figure 5:
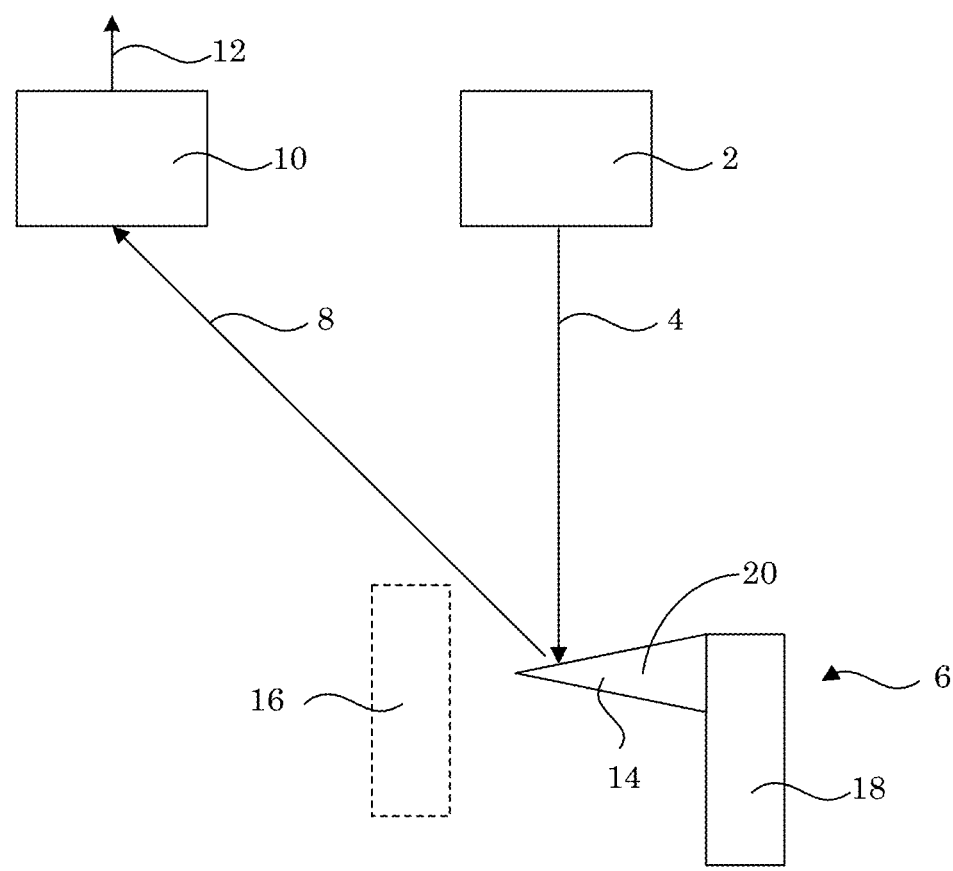
FIG. 5 shows an electron vibrometer.
Figure 6:
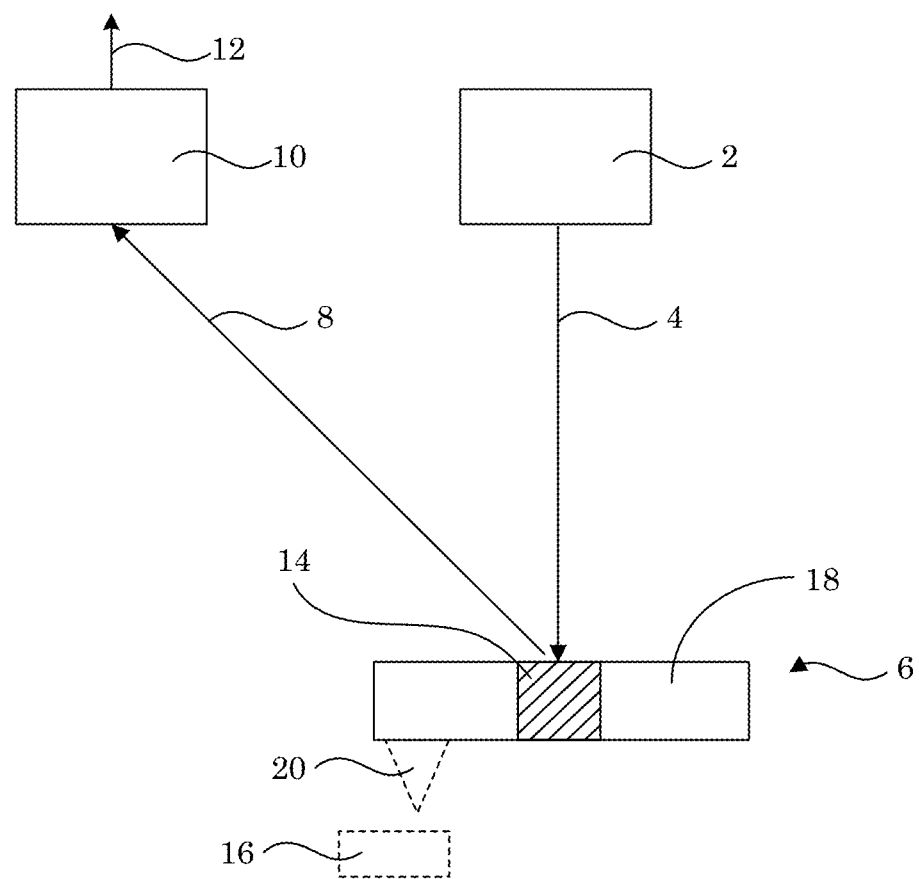
FIG. 6 shows an electron vibrometer.

In an embodiment, with reference to FIG. 5 and FIG. 6, scattered electrons 8 include secondary electrons, and charged particle detector 10 includes a secondary electron detector. Here, secondary electron detector 10 and electron source 2 are disposed on a same side of receiver portion 14 of cantilever 6.

Electron vibrometer 100 includes electron source 2 to provide the beam of primary electrons 4. Exemplary electron sources include field emission, thermionic, photoemission, and the like. In an embodiment, electron source 2 is the field emission. A diameter of the beam of primary electrons 4 at receiving portion 14 of cantilever 6 is from 0.1 nanometers (nm) to 1 micrometer (μm), specifically from 1 nm to 5 nm. In an embodiment, the diameter is from 1 nm to 10 nm.

An energy of primary electrons 4 can be from 100 electronvolts (eV) to 300 kiloelectronvolts (keV), specifically from 5 keV to 30 keV. A convergence half angle of primary electrons 4 from a central axis of the beam of primary electrons can be from 1 milliradian (mrad) to 30 mrad, specifically from 2 mrad to 10 mrad.

In some embodiments, the beam that is communicated to receiver portion 14 of cantilever 6 includes ions in an absence of primary electrons 4. Here, an ion vibrometer includes an ion source providing a beam of primary ions; cantilever 6 that includes receiver portion 14 (including a gradient in thickness, a gradient in mass, a gradient in atomic number of constituent atoms, or a combination of the foregoing gradients), cantilever 6 being disposed relative to the ion source such that receiver portion 14 of cantilever 6 receives the beam of primary ions, and produces a plurality of scattered ions from receiver portion 14 in response to receipt of the beam of primary ions; and charged particle detector 10 that receives the scattered ions from receiver portion 14. Moreover, charged particle detector 10 produces detector signal 12 that includes an amplitude that varies in relation to the gradient that is subject to receipt of the primary ions, and detector signal 12 provides determination of the displacement of cantilever 6. Here, receiver portion 14 of cantilever 6 oscillates relative to the beam of primary ions, ion source, charged particle detector 10, or a combination thereof. In an embodiment, cantilever 6 oscillates relative to the ion source.

Exemplary ion sources include liquid metal, gas field, and the like. In an embodiment, the ion source is the gas field. A diameter of the beam of primary ions at receiving portion 14 of cantilever 6 is from 0.3 nanometers (nm) to 1 micrometer (μm), specifically from 0.5 nm to 5 nm. In an embodiment, the diameter is from 1 nm to 25 nm.

An energy of the primary ions can be from 1 kiloelectronvolts (keV) to 100 keV, specifically from 5 keV to 50 keV. A convergence half angle of primary ions 4 from a central axis of the beam of primary ions can be from 0.1 milliradian (mrad) to 10 mrad, specifically from 0.1 mrad to 1 mrad. Exemplary primary ions include monatomic ions (e.g., noble gas ions (e.g., $He^+$, $Ne^+$, $Ar^+$), transition metal ions (e.g., $Cu^{2+}$, $Au^+$, $Co^{2+}$), alkali metal ions (e.g., $Li^+$, $Na^+$, $K^+$), alkaline earth metal ions (e.g., $Be^{2+}$, $Mg^{2+}$, $Ca^{2+}$), ions of p-block elements from the periodic table (e.g., $Ga^+$, $Al^+$, $In^+$), and the like, polyatomic ions, or a combination thereof. The primary ions can be singly charged, multiply charged, or a combination thereof. In an embodiment, the primary ions include $He^+$.

It is contemplated that electron vibrometer 100 or the ion vibrometer is disposed in a chamber in which a pressure in the chamber is effective to transmit the beam of primary electrons 4 (or primary ions in case of the ion vibrometer). The pressure in the chamber can be from $1\times10^{-10}$ Torr to 760 Torr, specifically from $1\times10^{-6}$ Torr to 760 Torr.

Cantilever 6 can be made, e.g., using a microfabrication or nanofabrication process used for making an article from a semiconductor such as silicon or a metal such as nickel. Cantilevers are commercially available with or without a tip. Cantilever 6 can be disposed on a mount and subjected to a stimulus, wherein cantilever 6 oscillates in response to the stimulus. The stimulus can be, e.g., vibration of cantilever 6, an applied potential (e.g., when cantilever 6 includes a piezoelectric material), and the like.

Cantilever 6 can have a variety of shapes including polygonal, frustoconical, cuboidal, triangular, V-shaped, D-shaped, and the like. A length L of the cantilever can be greater than or equal to a width W of the cantilever. The width W can be greater than or equal to a thickness of the cantilever. The length L of the cantilever can be from 0.05 micrometer (μm) to 1 mm, specifically from 0.1 μm to 5 μm. The width W of the cantilever can be from 0.01 μm to 500 μm, specifically from 0.05 μm to 2 μm. The thickness of the cantilever can be from 1 nm to 10 μm, specifically from 5 nm to 2 μm. A mass of cantilever 6 can be from $1\times10^{-9}$ nanogram (ng) to 30 micrograms (μg), specifically from $5\times10^{-8}$ ng to $5\times10^{-5}$ ng.

In various embodiments, cantilever 6 is present in an environment that includes a fluid (e.g., gas or liquid), solid, or a combination thereof at a temperature, e.g., from 1 Kelvin (K) to a maximum temperature permitted by the materials of components of cantilever 6, specifically from 1 K to 500 K, and more specifically from 1 K to 400 K.

Tip 20 of cantilever 6 can have a variety of shapes, including tetrahedral, rectangular pyramidal, conical, spherical, cylindrical, and the like.

In an embodiment, cantilever 6 has an apex at, e.g., tip 20 such that cantilever 6 interacts with sample 16 at the apex. Cantilever 6 can exhibit flexural bending or torsional bending in response to a force at the apex of tip 20. Moreover, cantilever 6 can exhibit a mechanical eigenmode in response to a time varying force.

Cantilever 6 includes receiver portion 14. Receiver portion 14 includes a gradient in a property. The property can be a thickness, mass, atomic number of the constituent atoms of the cantilever 6, or a combination thereof. Accordingly, the gradient in the property can be a gradient in thickness, a gradient in mass, a gradient in atomic number of constituent atoms, or a combination thereof. The gradient can be present in tip 20, body member 18, or a combination thereof of cantilever 6. In an embodiment, the gradient is the gradient in mass. Here, the gradient in mass can be a combination of compositional and geometrical variations achieved during fabrication. In an embodiment, the gradient is the gradient in atomic number. Here, the gradient in atomic number can be achieved through alloying. In an embodiment, the gradient is the gradient in material thickness. Here, the gradient in thickness can be created by microfabrication or nanofabrication.

Due to presence of receiver portion 14 of cantilever 6, the beam of primary electrons 4 (or primary ions) are scattered as scattered electrons 8 (or scattered ions), wherein a number density of scattered electrons 4 (or scattered ions) varies due to the gradient. With respect to the gradient in mass, a higher mass region of receiver portion 14 produces a lower number density of scattered electrons 4 as compared with a lower mass region of receiver portion 14. Similarly, with respect to the gradient in atomic number, a region of higher atomic number atoms in receiver portion 14 produces a lower number density of scattered electrons 4 as compared with a region of lower atomic number atoms in receiver portion 14. In this manner, a number density of scattered electrons 4 changes (e.g., increases or decreases) with the gradient. Accordingly, detector signal 12 changes (e.g., increases or decreases) with variation of the number density of scattered electrons 4 received at charged particle detector 10.

Charged particle detector 10 selectively detects arrival of scattered electrons 4 and has a shape of an active area or element for electron detection in which electrons that are not scattered electrons 4 are not detected. In an embodiment, a geometrical shape or format of charged particle detector 10 detects scattered electrons 8 from receiver portion 4 of cantilever 6 such that charged particle detector 10 detects a change in an amount (e.g., number density) of scattered electrons 8 due to displacement of cantilever 6.

Exemplary charged particles detectors include scintillators, solid state diodes, direct specimen current, and the like. In an embodiment, charged particles detectors 10 is the scintillator detector. Here, charged particles detectors 10 had scintillation material coupled to a photomultiplier tube that converts electrons to photons to photoelectrons.

It is contemplated that a thickness of material, atomic number, material density, and the like can be varied along a length of receiver portion 14 of cantilever 6 to change (e.g., modulate) the amount of scattered electrons 4 from cantilever 6.

Cantilever 6 is sensitive to a condition of sample 16 probed by cantilever 6. Exemplary conditions include electron density, surface corrugation, surface stiffness, electrical conductivity, magnetic force, topography, atomic arrangement, surface defect, mechanical contact force, van der Wags force, capillary force, chemical bonding, electrostatic force, Casimir force, solvation force, and the like. A construction and arrangement of cantilever 6 in combination with sample 16 can be varied and adapted for various geometries and uses.

The sample can be solid surfaces, nanoparticles, biomolecules and the like.

In an embodiment, a process for making electron vibrometer 100 includes providing electron source 2; disposing charged particle detector 10 to receive scattered electrons 8; and disposed cantilever 6 such that receiver portion receives the beam of primary electrons 4 from electron source 2 and produces scattered electrons 8 in response to receipt of primary electrons 4 from electron source 2. According to an embodiment, disposing charged particle detector 10 includes disposing charged particle detector 10 on a same side of receiver portion 14 as electron source 2, wherein charged particle detector 10 is a secondary electron detector, and scattered electrons 8 are secondary electrons. According to an embodiment, disposing charged particle detector 10 includes interposing receiver portion 14 between charged particle detector 10 and electron source 2, wherein charged particle detector 10 is a transmitted electron detector, and scattered electrons 8 are transmitted electrons.

Electron vibrometer 100 has numerous beneficial uses, including determining displacement of cantilever 6. In an embodiment, a process for determining a displacement of a cantilever includes providing the beam of primary electrons 4; subjecting cantilever 6 at receiver portion 14 to the beam of primary electrons 4, cantilever 6 including: receiver portion 14 that includes a gradient in thickness, a gradient in mass, a gradient in atomic number of constituent atoms, or a combination comprising at least one of the foregoing gradients; receiving the beam of primary electrons 4 at receiver portion 14 of cantilever 6; producing a plurality of scattered electrons 8 from receiver portion 14 in response to receiving the beam of primary electrons 14; receiving scattered electrons 8 at charged particle detector 10; and producing, by charged particle detector 10, detector signal 10 including an amplitude that varies in relation to the gradient present in receiver portion 14 to determine the displacement of cantilever 6.

In the process, providing the beam of primary electrons 4 includes aligning the beam with the receiver portion 14.

Here, detector signal 10 can be analyzed to provide the displacement of cantilever 6 by measuring the intensity of the transmitted electron signal with time.

In an embodiment, a process for acquiring a condition of a sample includes providing sample 16 proximate to cantilever 6; adjusting a distance between cantilever 6 and sample 16; probing sample 16 with cantilever 6; displacing cantilever 6 in response to a condition of sample 16; communicating displacement of cantilever 6 to charged particle detector 10 by producing scattered electrons 8 from primary electrons 4, and detecting (by charged particle detector 10) the displacement of cantilever 6 to acquire the condition of sample 16. The condition of sample 16 can include, e.g., an electron density, surface corrugation, surface stiffness, electrical conductivity, magnetic force, topography, atomic arrangement, surface defect, mechanical contact force, van der Wags force, capillary force, chemical bonding, electrostatic force, Casimir force, solvation force, or a combination thereof. It is contemplated that scattered electrons 8 can include secondary electrons or transmitted electrons, or a combination thereof, wherein detection of secondary electrons and transmitted electrons respectively involves a secondary electron detector and transmitted electron detector as charged particle detectors.

Electron vibrometer 100 has numerous advantageous and beneficial properties. Electron vibrometer 100 allows displacement measurements to be made on cantilevers 3 orders of magnitude smaller and faster than optical methods.

Advantageously and unexpectedly, the lower bound of detection limit is smaller than the ion or electron beam diameter and the magnitude of the signal increases as the receiver portion is made smaller.

The articles and processes herein are illustrated further by the following Example, which is non-limiting.

EXAMPLE

Detection of Atomic Force Microscopy Cantilever Displacement with an Electron Vibrometer.

A response time of an atomic force microscopy (AFM) cantilever can be decreased by reducing cantilever size;

however, the fastest AFM cantilevers are currently nearing the smallest size that can be detected with the conventional optical lever approach. An electron vibrometer measures AFM cantilever displacements. The oscillating AFM tip is positioned perpendicular to and in the path of a stationary focused nanometer sized beam of primary electrons. As the tip oscillates, the thickness of material exposed to the primary electrons changes and produces a change in the number of scattered electrons that are detected. Detection of sub-nanometer vibration amplitudes with the beam of primary electrons is shown, providing a pathway for dynamic AFM with cantilevers that are orders of magnitude smaller and faster than the current state of the art.

The electron vibrometer overcome limitations of conventional optic sensing of cantilever displacement and provides improvement in imaging speed. The response time of the AFM cantilever is inversely proportional to the cantilever resonance frequency $\omega$. The value of $\omega$ is proportional to the square root of the ratio of cantilever stiffness k to cantilever mass m. Thus, improved response time can be achieved by increasing k or by decreasing m. Substituting geometric parameters of a rectangular cantilever and isotropic material properties for k and m provides formula 1.

$$\omega \propto \sqrt{\frac{k}{m}} \propto \frac{h}{L^2}\sqrt{\frac{E}{\rho}}, \quad (1)$$

Here, h is cantilever thickness, L is cantilever length, E is cantilever Young's modulus, and $\rho$ is cantilever material density. For a rectangular cantilever, k is related to geometric parameters and material properties as in formula 2.

$$k = \frac{Eb}{4}\left(\frac{h}{L}\right)^3 \quad (2)$$

Here, b is the width of the AFM cantilever. Formulas 1 and 2 show that by decreasing L while holding h/L constant, $\omega$ can be increased while k remains constant. By reducing cantilever lengths to sub-micrometer dimensions, orders of magnitude improvement in speed is provided.

In the electron vibrometer, the beam of primary electrons provides detection of displacement of the AFM cantilever. The beam of primary electrons can be focused into a spot size ~100 times smaller than an optical beam, and provide detection of displacement of much smaller and faster oscillating AFM cantilevers.

Figure 7:
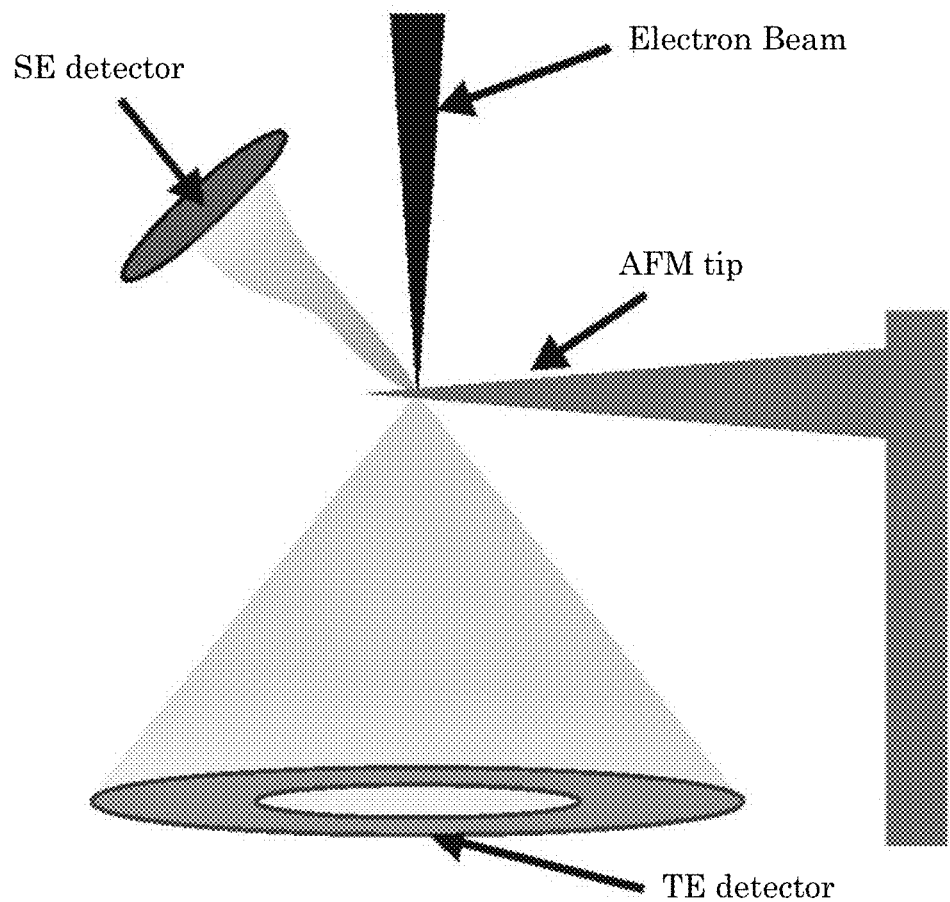
FIG. 7 shows an electron vibrometer.

An AFM cantilever (NCL, Nanosensors, Germany) mounted on a holder (Dimension 3000, Digital Instruments, Santa Barbara, Calif.) containing a piezoelectric actuator was inserted into a field emission scanning electron microscope (FESEM, Leo Gemini 1525, Carl Zeiss AG, Germany) operating at a beam current of 150 pA and an accelerating voltage of 30 kV. At 30 kV Monte Carlo simulations of electron scattering predict more than 99% of electrons will be transmitted through a 200 nm thick section of silicon, maximizing the detected signal. For the same conditions, a temperature rise of less than $10^{-3}$ K is predicted from inelastic scattering, suggesting that local heating of the AFM tip is negligible. The AFM tip was positioned such that it was under the electron beam and perpendicular to the optic axis of the FESEM as shown in FIG. 7. The focused electron beam size for this instrument was approximately 3 nm to 5 nm. We performed electron detection with two different detectors: a solid-state silicon diode transmitted electron (TE) detector (KE Developments, Deben, UK) and a scintillator-based backscatter electron detector (Robinson, ETP Semra, Australia). The scintillator backscatter detector was employed as a TE detector by placing it below the sample with the active detector area facing up (cf. FIG. 7). Both electron detectors were positioned such that they collected scattered transmitted electrons and allowed unscattered electrons to pass through a hole on the optic axis. In this configuration these detectors produced dark-field (DF) images. The signal used for electron detection of cantilever displacements was the output video voltage from the electron detector amplifier, which was measured with an oscilloscope (Virtual Bench, National Instruments, Austin, Tex., e.g. FIG. 2b, 3a) or a lock-in amplifier (7280, Signal Recovery, Oak Ridge, Tenn., e.g. FIG. 2c, 3b, 3c). The output video voltage from the electron detector amplifier, which will be referred to as the output signal, is the voltage conventionally used to form the digital image on the SEM computer and is typically on the order of hundreds of millivolts.

Figure 8:
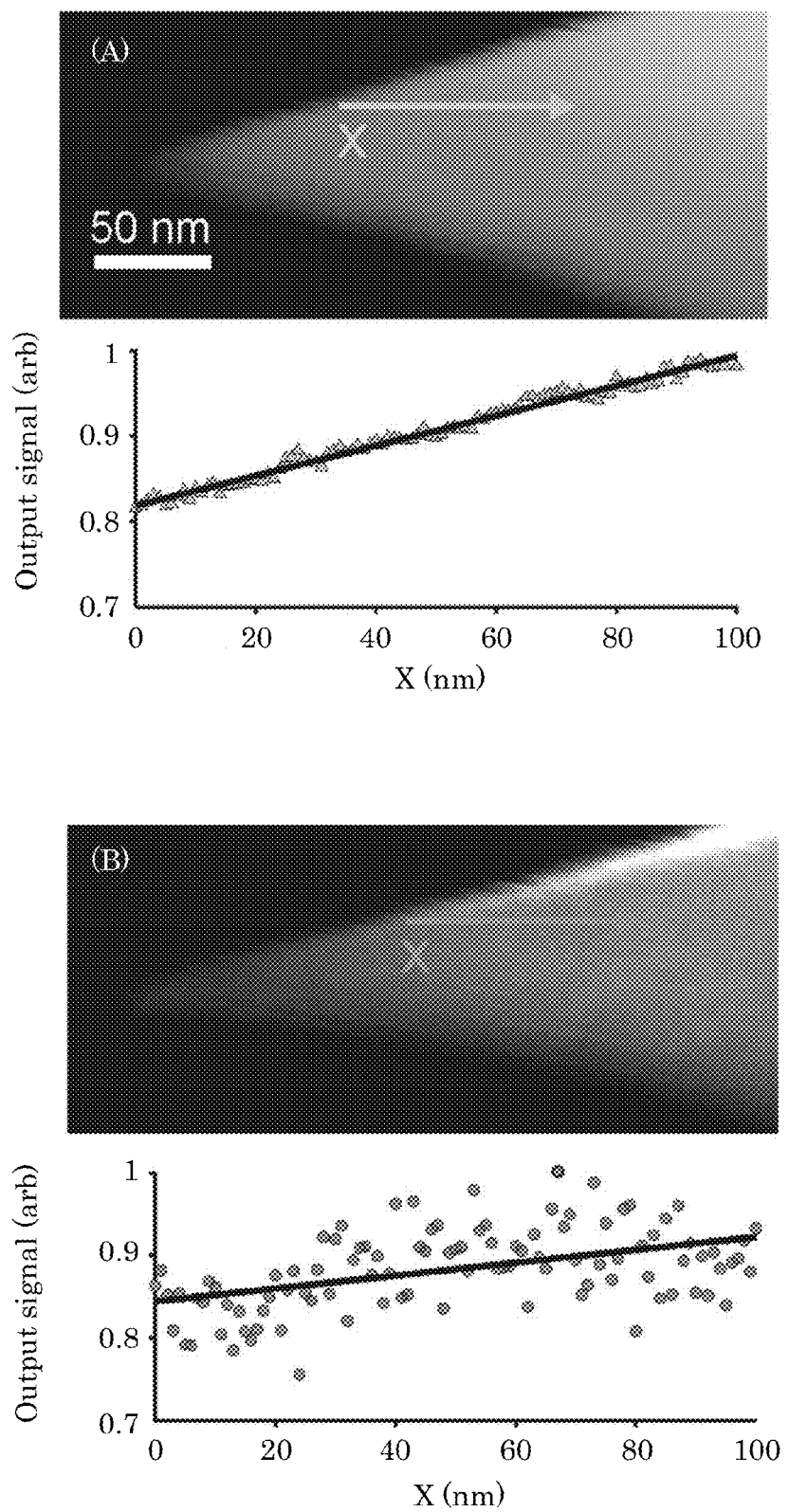
FIG. 8 shows an image of a tip of cantilever in panel A; panel B shows a graph of detector signal versus position along the tip in panel A; panel C shows an image of a tip of cantilever, and panel D is a graph of detector signal versus position along the tip in panel C.

The gradient in material thickness along the length of the AFM tip produces a variation in the output signal that can be used to detect cantilever vibrations. Panel A of FIG. 8 shows a DF-TE image of the AFM tip recorded with the solid state silicon diode detector. The plot of (normalized) DF-TE output signal shows a linear increase of 20% for a 100 nm displacement along the AFM tip (slope of $1.8 \times 10^{-3}$, goodness of fit $R^2=0.983$). The scintillator TE detector produced similar DF-TE images (cf. FIG. 9). The DF-TE image contrast is explained by the mass-thickness contrast mechanism described by:

$$\frac{N}{N_0} = 1 - \exp\left(-\frac{T\sigma\rho N_A}{W}\right). \quad (3)$$

Figure 12:
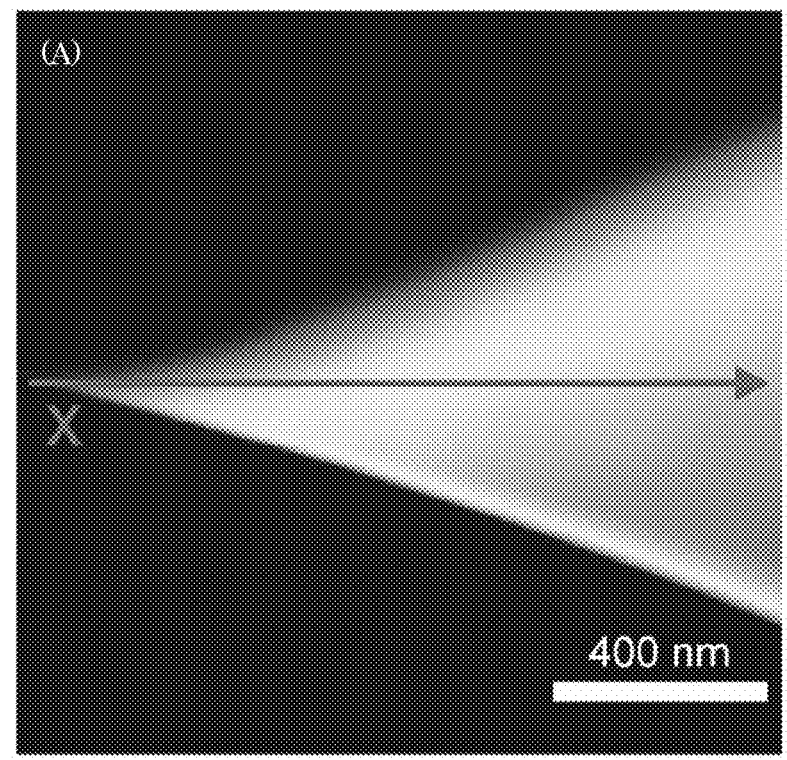
FIG. 12 shows an image of a tip of a cantilever, and panel B shows a graph of detector signal versus position along tip shown in panel C.
Figure 12:
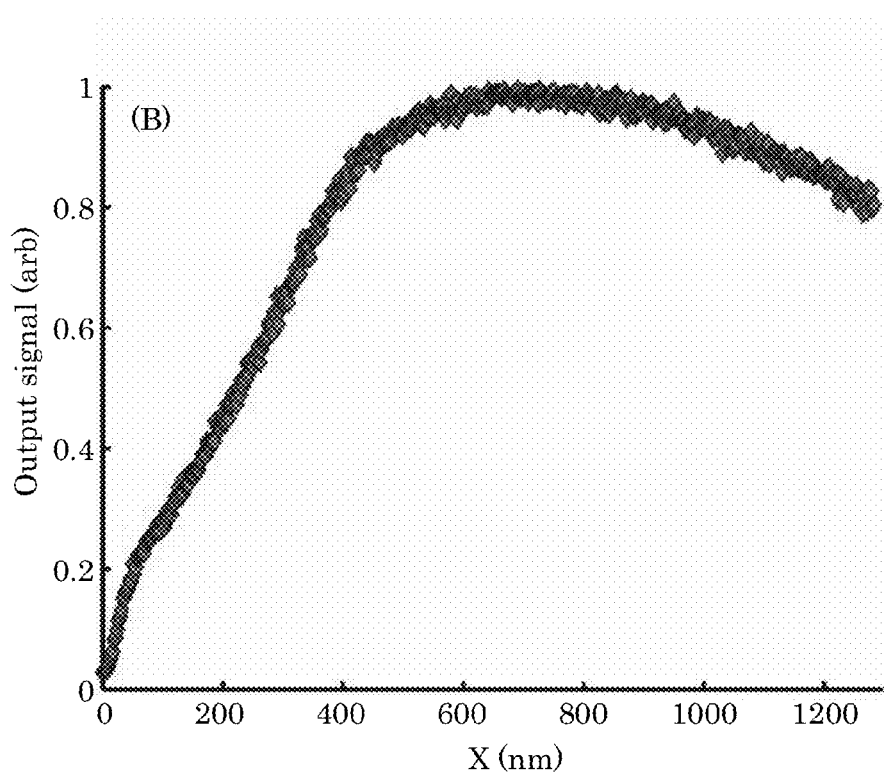

Here, N is the number of transmitted electrons scattered to the DF detector by the sample, $N_0$ is the number of incident electrons, T is the material thickness, $\sigma$ is the scattering cross section of the material, $\rho$ is the material density, $N_A$ is Avogadro's number, and W is the atomic weight of the material. FIG. 12 shows the inverse exponential dependence predicted by formula (3) for displacements of ~1 µm along the AFM tip. The first-order term in the Taylor series expansion of formula (3) around T is:

$$\frac{N}{N_0} \approx \frac{T\sigma\rho N_A}{W}. \quad (4)$$

The ratio, $$\frac{N}{N_0},$$

is proportional to the detector output signal, with the brightness and contrast of the image as proportionality constants. Given the linear thickness gradient of the AFM tip, the linear relationship observed in panel A of FIG. 8 is reasonable for small changes in the position of the AFM tip relative to the electron beam.

In the SEM, secondary electron (SE) imaging is more common than TE imaging. We compared the output signal obtained with a conventionally-positioned Everhart-Thornley SE detector to that obtained with TE detection. Panel B of FIG. 8 shows an SE image of the AFM tip, with a corresponding plot of SE output signal (normalized to the maximum) along the green line in the image. The SE signal increases approximately 5% for a 100 nm displacement along the AFM tip with a fitted slope of $7.75\times10^{-4}$, albeit with a significant amount of noise and weak linear dependence ($R^2$=0.22). The TE image in panel A of FIG. 8 has an order of magnitude less error in the linear fit compared to the SE image. Based on the linear relationship between output signal and displacement for small displacements and the low noise and larger slope relative to SE imaging, we conclude that the TE signal is superior for thickness-based detection of AFM cantilever vibration.

Figure 9:
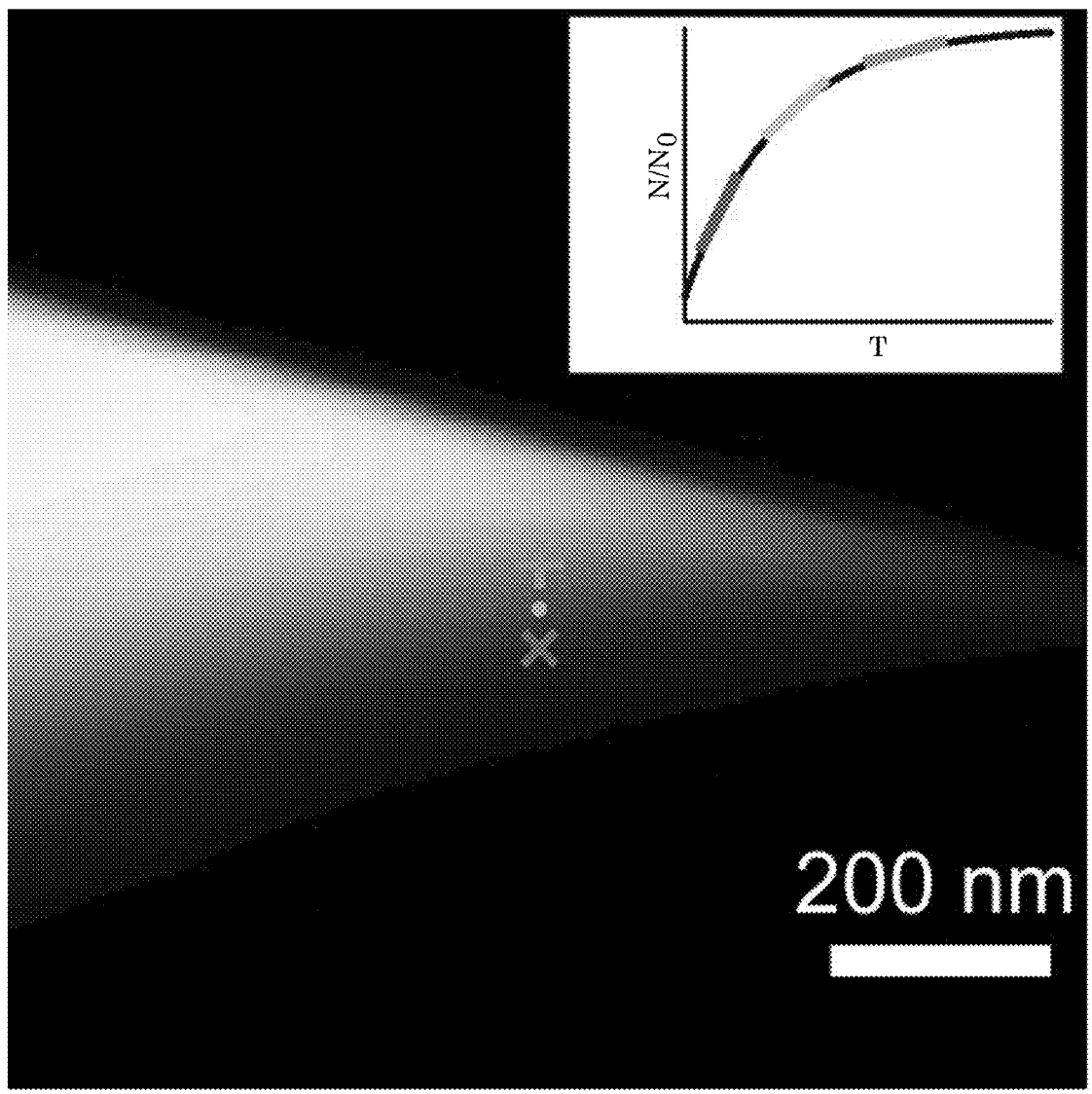
FIG. 9 shows an image of a tip of a cantilever, wherein the inset shows a graph of normalized number of transmitted electrons (N/NO) versus thickness T of the tip.
Figure 10:
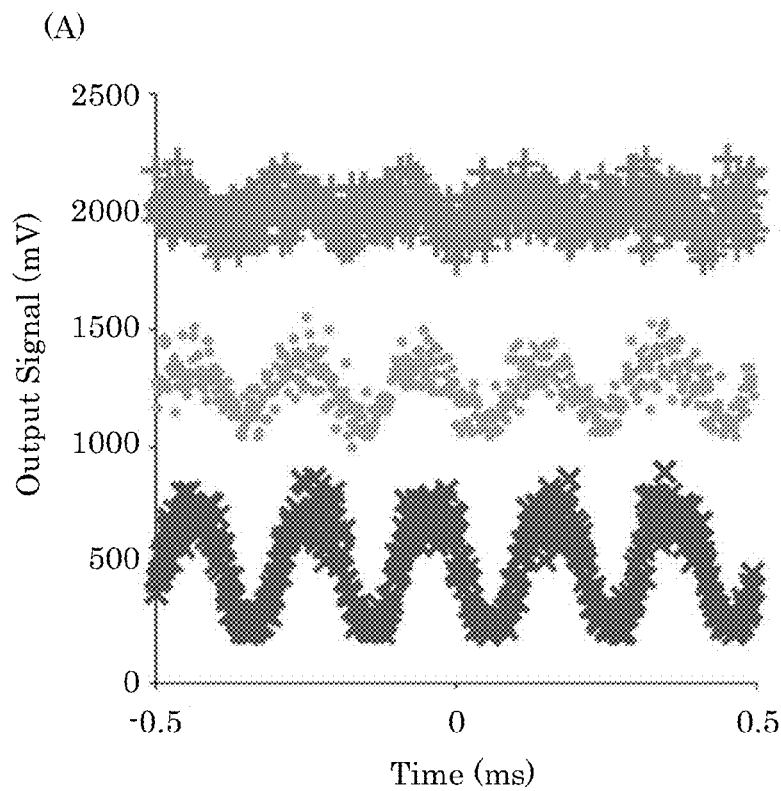
FIG. 10 shows a graph of detector signal versus time, and panel B shows a graph of amplitude versus drive voltage.
Figure 10:
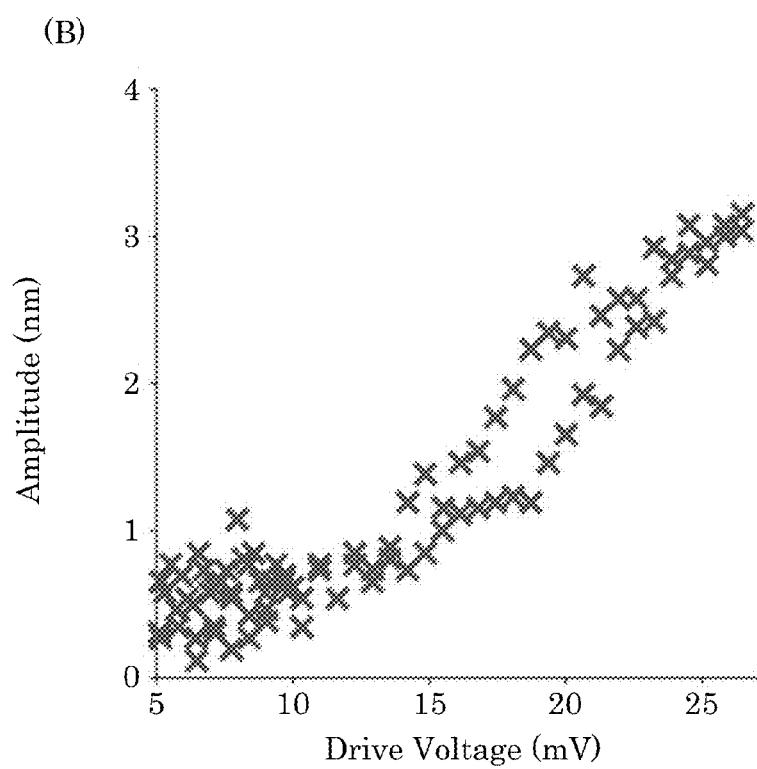
Figure 13:
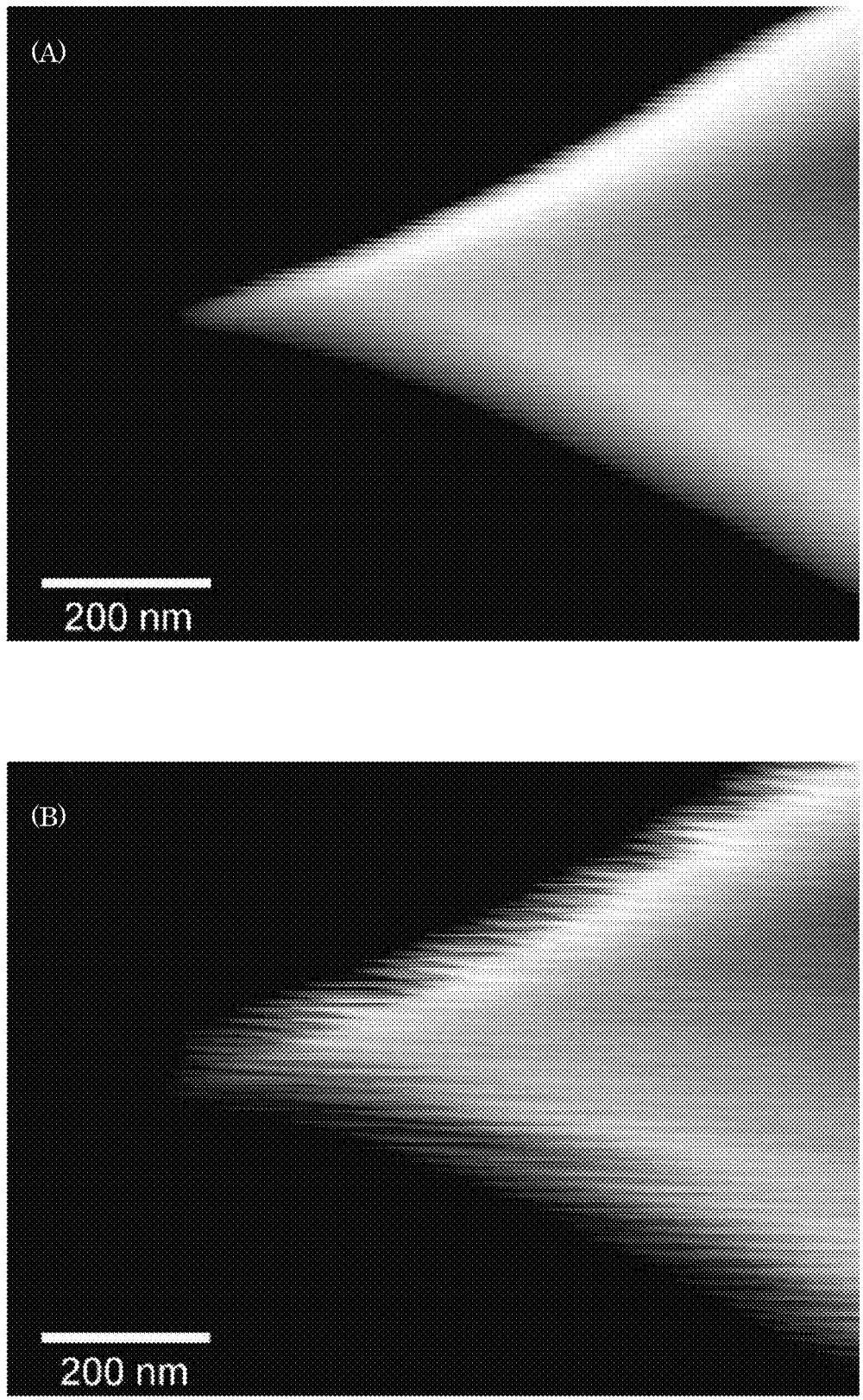
FIG. 13 shows an image of a tip of a cantilever in a static position, and panel B shows an image of a tip of a cantilever subject to vibration.

Dynamic AFM operation includes detection of a vibrating AFM cantilever as opposed to the stationary cantilever shown in FIG. 7. To demonstrate this, we acquired a DF-TE image of the AFM tip and used this image to position a stationary electron beam on the tip in spot mode. We then provided a sinusoidal drive voltage to the piezoelectric actuator in the cantilever holder and monitored the output signal of the TE detector (see FIG. 13 for TE SEM images of the tip with and without drive voltage applied). FIG. 9 and panel A of FIG. 10 show the position of the stationary electron beam and the corresponding output signal for three different detection positions for an AFM cantilever oscillating at 5 kHz with a drive voltage of 1414 mV, which produced a vibration amplitude of approximately 200 nm. The amplitude of the output signal was largest when the electron beam was placed near the edge of the AFM tip (red x, FIG. 9 and panel A of FIG. 10) and decreased when the electron beam was placed closer to the center of the tip (blue diamond and green cross, FIG. 9 and panel A of FIG. 10). As qualitatively shown in the inset in FIG. 9, the sensitivity of the output signal to vibrations decreases with increasing material thickness due to the exponential dependence of $$\frac{N}{N_0}$$

on material thickness (formula (3) and FIG. 9 inset). The signal to noise ratio SNR, calculated from the power spectral density of the time domain data in panel A of FIG. 10, improves from 6.9 at the green cross to 18.9 at the blue dot, to 45.1 at the red x. The improvement in SNR when moving the electron beam to thinner portions of the tip suggests a pathway towards better SNR by optimizing the geometry of the tip and the position of the beam. Combined with the mass-thickness electron scattering theory, this experiment demonstrates that the absolute material thickness associated with the position of the detecting electron beam determines the sensitivity of the measurement and shows that placement of the electron beam near the edge of the AFM tip produces the most sensitivity to cantilever displacements.

Because the electron beam position on the AFM tip can be controlled and the beam has a calibrated position, calibration of the displacement of the AFM tip is possible. To calibrate the relationship between output signal and cantilever displacement, we scanned the electron beam along a 200 nm horizontal line near the red x in FIG. 9 on a stationary AFM tip and measured the output signal with an oscilloscope. From the slope of the output signal and known length of the electron beam scan, we determined the sensitivity of the electron detection near the red x to be (1.3±0.4) mV/nm (all uncertainties are reported to the 95% confidence interval). The detection sensitivity will depend specifically on the location of the beam spot, the electron detector brightness and contrast settings, and the shape and composition of the AFM tip, which can change over time due to carbon buildup and amorphization. The average power spectral density of the calibrated output signal near the red x in the bandwidth of 10 kHz to 250 kHz was measured to be 0.1 nm/$\sqrt{\text{Hz}}$. This value is higher than for modern commercial AFM instruments and will need to be reduced to achieve high performance imaging. The noise floor is strongly dependent on the local thickness of the AFM tip, and can be improved with optimization of the electron detection system including better positional stability, allowing positioning of the electron beam on thinner portions of the tip.

We increased the amplitude of the drive voltage while the electron beam was positioned near the red x in FIG. 9 and measured the amplitude of the cantilever displacement with the lock-in amplifier. From the measured sensitivity and the drive amplitude ramp in panel B of FIG. 10, we concluded that with a lock-in time constant of 10 ms the minimum detectable amplitude at a frequency of 5 kHz was 0.9 nm. High-speed imaging will require faster lock-in time constants to coincide with higher pixel acquisition rates. At the current noise levels, increasing the resonance frequency will proportionally decrease the integration time required to average a fixed number of displacement cycles. The thermal noise limit will also be improved with higher frequency cantilevers because the noise is distributed over a wider frequency band. Furthermore, by improving the SNR in the measurement, the number of displacements for precise amplitude measurement decreases.

Figure 11:
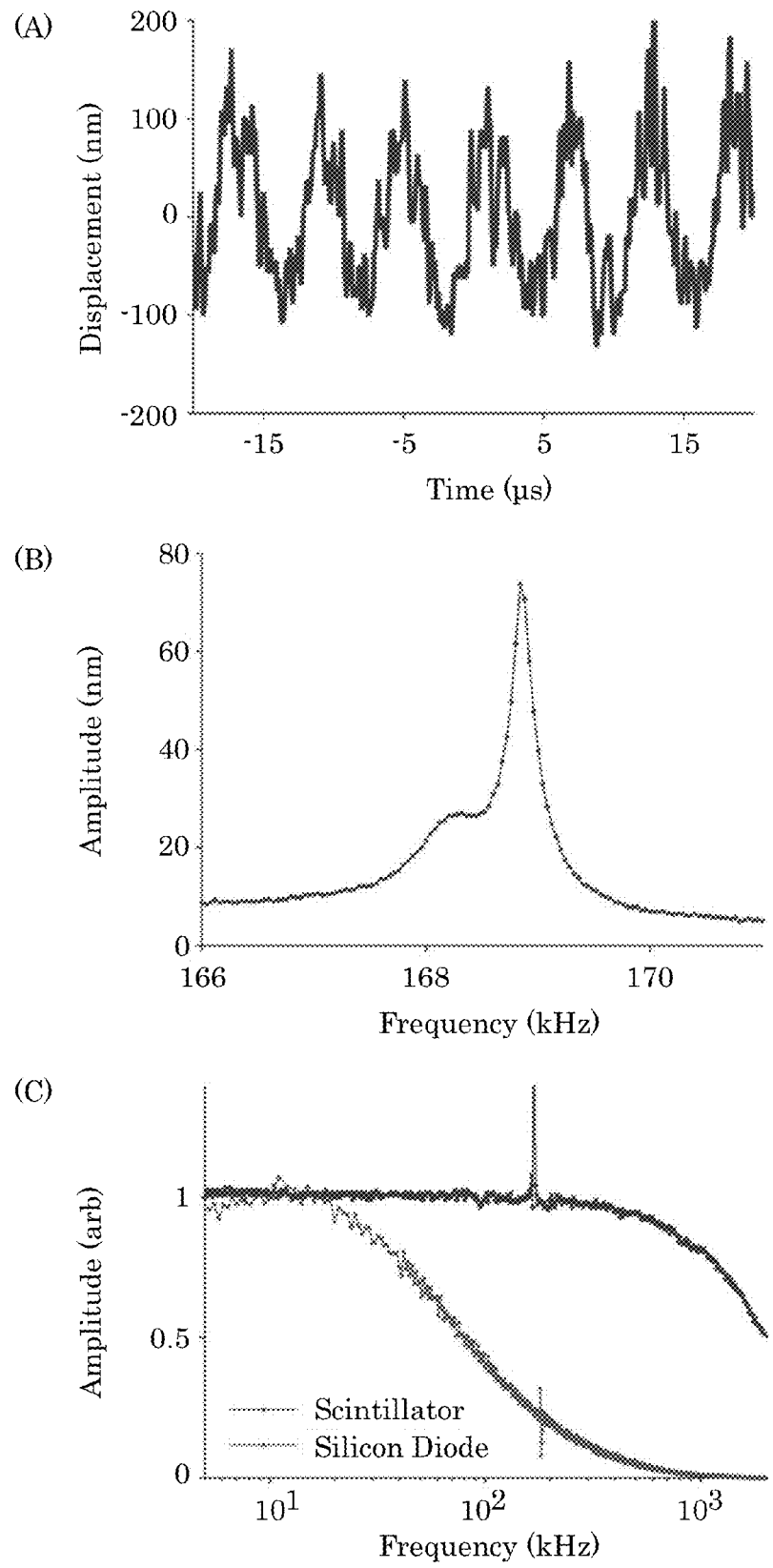
FIG. 11 shows a graph of displacement versus time in panel A; panel B shows a graph of amplitude versus time, and panel C shows a graph of amplitude versus frequency.

Frequency sweep experiments over the electron detector bandwidth demonstrated the ability to measure the resonant frequency of an AFM cantilever and demonstrated the role of the electron detector bandwidth in limiting the measurable frequency range. Panel A of FIG. 11 shows the on-resonance cantilever displacement over several oscillation periods at a drive frequency of 168.85 kHz and a drive amplitude of 141.4 mV. The amplitude of the displacement while the drive frequency was swept through the cantilever resonance is shown in panel B of FIG. 11. This result demonstrates that the dynamic motion of the AFM cantilever at and near resonance can be detected with the TE electron signal. Observation of this resonance peak confirms that the output signal is not the product of a stray electric field from driving the piezoelectric actuator because this resonance peak is a property of the mechanical motion of the AFM cantilever. Panel C of FIG. 11 compares the normalized amplitude of the scintillator and silicon diode detector output signals for long range frequency sweeps on two different cantilevers of the same type. The scintillator detector had a cut off frequency (3 dB bandwidth) of (1300±20) kHz and the silicon diode detector had a cut off frequency of (43±2) kHz. Therefore, for the specific detectors used in these experiments, the scintillator detector is better for higher frequency measurements. Nonetheless, the scintillator detector is still not operating close to its theoretical response time, which is on the order of nanoseconds. This suggests that post-detector electronics were responsible for the roll off observed in panel C of FIG. 11. An optimized detector for this technique has faster post-detector electronics allowing for higher detector cut off frequencies.

Figure 14:
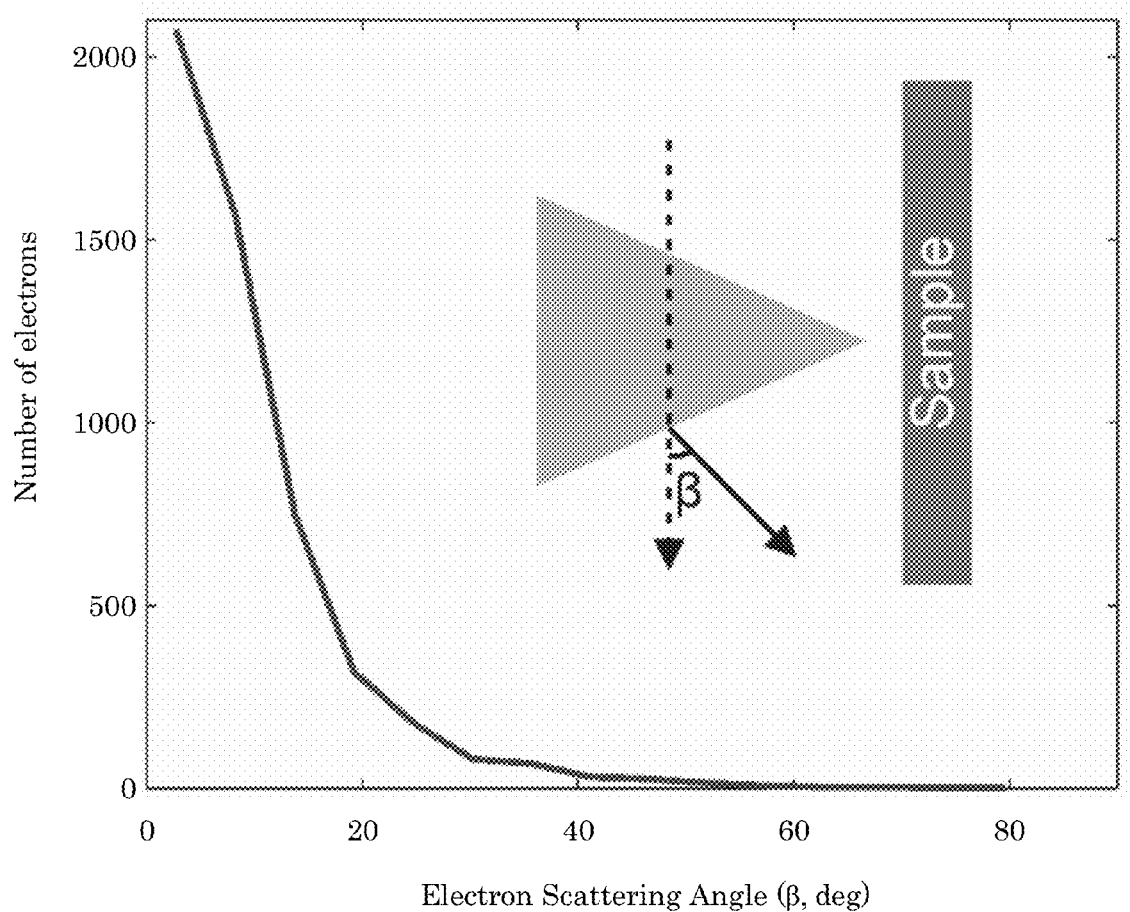
FIG. 14 shows a graph of number of electrons versus electron scattering angle.

Sample roughness and sample tilt may affect the ability of the electron beam to access the tip in a side-illumination configuration. Substrates can be smooth, and relative sample and beam tilt can be carefully adjusted in the SEM. Placing a separate tip for electron detection on the backside of the cantilever can occur further from the sample surface. A second sample consideration is the interaction between the scattered electrons and fragile specimens. A Monte Carlo simulation (see FIG. 14) of electron scattering through a 150 nm thick section of the tip indicated that fewer than 0.1% of transmitted electrons scattered to angles greater than 60° (where 90° represents the sample directly beneath the tip). This suggests that a sample area on the order of hundreds of nanometers in diameter surrounding the tip-sample contact point, which would include the scan area, is shadowed and protected from electron irradiation due to the scattering angles of the transmitted electrons.

We have demonstrated the detection of AFM cantilever vibrations with the electron vibrometer. Calibration relates electron detector output to absolute displacement of the tip. Electron scattering theory and experiments using different electron beam detection positions on the AFM tip showed that the sensitivity of the detection method increased with decreasing material thickness. Long-range frequency sweeps indicated that the scintillator detector used had an operating frequency of 1300 kHz. The advantage of the electron vibrometer is the downward scalability of cantilever size by orders of magnitude. Smaller AFM cantilevers are faster and can retain low stiffness to measure fragile samples as compared with conventional optical sensing of displacement of the cantilever.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An electron vibrometer to determine a displacement of a cantilever, the electron vibrometer comprising:
   an electron source providing a beam of primary electrons;
   the cantilever comprising:
      a receiver portion comprising:
         a gradient in mass, a gradient in thickness, a gradient in atomic number of constituent atoms, or a combination comprising at least one of the foregoing gradients,
      the cantilever being disposed relative to the electron source such that the receiver portion of the cantilever receives the beam of primary electrons, and produces a plurality of scattered electrons from the receiver portion in response to receipt of the beam of primary electrons; and
   a charged particle detector that receives the plurality of scattered electrons from the receiver portion, and produces a detector signal comprising an amplitude that varies in relation to the gradient subject to receipt of the primary electrons, and the detector signal providing determination of the displacement of the cantilever.

2. The electron vibrometer of claim 1, further comprising a sample disposed proximate to the cantilever and arranged to interact with the cantilever.

3. The electron vibrometer of claim 1, wherein:
   the cantilever further comprises:
      a body member; and
      a tip disposed on the body member.

4. The electron vibrometer of claim 3, wherein the tip comprises the receiver portion.

5. The electron vibrometer of claim 3, wherein the body member comprises the receiver portion.

6. The electron vibrometer of claim 1, wherein the beam of primary electrons comprises a beam diameter that is from 1 nanometer (nm) to 500 nm.

7. The electron vibrometer of claim 1, wherein the charged particle detector comprises a scintillator, a solid state diode, a specimen current, or a combination comprising at least one of the foregoing charged particle detectors.

8. The electron vibrometer of claim 1, wherein the scattered electrons comprise transmitted electrons, secondary electrons, or a combination comprising at least one of the foregoing scattered electrons.

9. The electron vibrometer of claim 8, wherein the scattered electrons comprise the transmitted electrons, and
   the charged particle detector comprises a transmitted electron detector.

10. The electron vibrometer of claim 9, wherein the transmitted electron detector is disposed opposing the electron source, and the receiver portion is interposed between the electron source and the transmitted electron detector.

11. The electron vibrometer of claim 8, wherein the scattered electrons comprise the secondary electrons, and the charged particle detector comprises a secondary electron detector.

12. The electron vibrometer of claim 11, wherein the secondary electron detector and the electron source are disposed on a same side of the receiver portion.

13. A process for determining a displacement of a cantilever, the process comprising:

providing a beam of primary electrons;

subjecting the cantilever at a receiver portion to the beam of primary electrons, the cantilever comprising:

the receiver portion comprising:

a gradient in mass, a gradient in thickness, a gradient in atomic number of constituent atoms, or a combination comprising at least one of the foregoing gradients, receiving the beam of primary electrons at the receiver portion of the cantilever;

producing a plurality of scattered electrons from the receiver portion in response to receiving the beam of primary electrons;

receiving the scattered electrons at a charged particle detector; and producing, by the charged particle detector, a detector signal comprising an amplitude that varies in relation to the gradient present in the receiver portion to determine the displacement of the cantilever.

14. The process of claim 13, further comprising interacting a sample with the cantilever.

15. The process for determining a displacement of a cantilever of claim 13, wherein:

the cantilever further comprises:

a body member; and a tip disposed on the body member.

16. The process for determining a displacement of a cantilever of claim 15, wherein the tip comprises the receiver portion.

17. The process for determining a displacement of a cantilever of claim 15, wherein the body member comprises the receiver portion.

18. The process for determining a displacement of a cantilever of claim 13, wherein the beam of primary electrons comprises a beam diameter that is from 1 nanometer (nm) to 500 nm.

19. The process for determining a displacement of a cantilever of claim 13, wherein the scattered electrons comprise the transmitted electrons;

the charged particle detector comprises a transmitted electron detector;

the transmitted electron detector is disposed opposing the electron source, and the receiver portion is interposed between the electron source and the transmitted electron detector.

20. The process for determining a displacement of a cantilever of claim 13, wherein the scattered electrons comprise the secondary electrons;

the charged particle detector comprises a secondary electron detector, and the secondary electron detector and the electron source are disposed on a same side of the receiver portion.

* * * * *